United States Patent
Glauser et al.

(10) Patent No.: US 8,501,079 B2
(45) Date of Patent: *Aug. 6, 2013

(54) CONTROLLING CRYSTALLINE MORPHOLOGY OF A BIOABSORBABLE STENT

(75) Inventors: Thierry Glauser, Redwood City, CA (US); Vincent Gueriguian, San Francisco, CA (US); Bethany Steichen, San Francisco, CA (US); James Oberhauser, Saratoga, CA (US); Manish Gada, Santa Clara, CA (US); Lothar Kleiner, Los Altos, CA (US); Mary Beth Kossuth, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 91 days.

This patent is subject to a terminal disclaimer.

(21) Appl. No.: 12/559,400

(22) Filed: Sep. 14, 2009

(65) Prior Publication Data
US 2011/0062638 A1    Mar. 17, 2011

(51) Int. Cl.
*B29C 55/26*    (2006.01)
*B29C 35/00*    (2006.01)

(52) U.S. Cl.
USPC .......................................... 264/573; 264/345

(58) Field of Classification Search
USPC .................. 264/171.26, 178 R, 209.1, 209.3, 264/209.4, 209.5, 211, 211.13, 235, 346, 264/514, 515, 519–521, 523, 534, 540, 563, 264/564, 567, 532, 535, 573
See application file for complete search history.

(56) References Cited

U.S. PATENT DOCUMENTS

| | | | |
|---|---|---|---|
| 3,636,956 A | 1/1972 | Schneider |
| 4,547,416 A | 10/1985 | Reed et al. |
| 4,698,196 A | 10/1987 | Fabian et al. |
| 4,702,884 A | 10/1987 | Goldstein |
| 4,957,687 A | 9/1990 | Akman et al. |
| 4,987,025 A | 1/1991 | Shiraki et al. |
| 5,087,394 A | 2/1992 | Keith |
| 5,108,416 A | 4/1992 | Ryan et al. |
| 5,116,365 A | 5/1992 | Hillstead |
| 5,147,302 A | 9/1992 | Euteneuer et al. |
| 5,500,013 A | 3/1996 | Buscemi et al. |
| 5,628,786 A | 5/1997 | Banas et al. |
| 5,670,161 A | 9/1997 | Healy et al. |
| 5,891,386 A | 4/1999 | Deitermann et al. |
| 6,360,577 B2 | 3/2002 | Austin |
| 6,500,146 B1 | 12/2002 | Pinchuk et al. |
| 6,572,813 B1 | 6/2003 | Zhang et al. |

(Continued)

FOREIGN PATENT DOCUMENTS

| EP | 0 583 170 | 2/1994 |
|---|---|---|
| EP | 1 800 628 | 6/2007 |

(Continued)

OTHER PUBLICATIONS

U.S. Appl. No. 10/956,911, filed Sep. 30, 2004, Durcan.

(Continued)

*Primary Examiner* — Ryan Ochylski
(74) *Attorney, Agent, or Firm* — Squire Sanders (US) LLP

(57) ABSTRACT

Methods to expand polymer tubing with desirable or optimum morphology and mechanical properties for stent manufacture and fabrication of a stent therefrom are disclosed.

3 Claims, 21 Drawing Sheets

(56) References Cited

U.S. PATENT DOCUMENTS

| | | |
|---|---|---|
| 6,626,939 B1 | 9/2003 | Burnside et al. |
| 6,645,422 B2 | 11/2003 | Jung et al. |
| 7,066,952 B2 | 6/2006 | Igaki |
| 7,070,615 B1 | 7/2006 | Igaki |
| 7,083,639 B2 | 8/2006 | Guinan et al. |
| 7,128,868 B2 | 10/2006 | Eidenschink |
| 8,002,817 B2 | 8/2011 | Limon |
| 2001/0014821 A1 | 8/2001 | Juman et al. |
| 2002/0041059 A1 | 4/2002 | Jung et al. |
| 2002/0077592 A1 | 6/2002 | Barry |
| 2002/0138133 A1 | 9/2002 | Lenz et al. |
| 2002/0151965 A1 | 10/2002 | Roth |
| 2003/0028241 A1 | 2/2003 | Stinson |
| 2003/0028246 A1 | 2/2003 | Palmaz et al. |
| 2003/0055488 A1 | 3/2003 | Igaki |
| 2003/0083732 A1 | 5/2003 | Stinson |
| 2003/0187158 A1 | 10/2003 | Preuschen et al. |
| 2003/0208254 A1 | 11/2003 | Shortt |
| 2003/0226833 A1 | 12/2003 | Shapovalov et al. |
| 2004/0000361 A1 | 1/2004 | Trozera |
| 2004/0098090 A1 | 5/2004 | Williams et al. |
| 2005/0004663 A1 | 1/2005 | Llanos et al. |
| 2005/0137678 A1 | 6/2005 | Varma |
| 2005/0177130 A1 | 8/2005 | Konstantino et al. |
| 2005/0187615 A1 | 8/2005 | Williams et al. |
| 2005/0196485 A1 | 9/2005 | Cass et al. |
| 2006/0020330 A1 | 1/2006 | Huang et al. |
| 2006/0076708 A1* | 4/2006 | Huang et al. .................. 264/239 |
| 2006/0211952 A1 | 9/2006 | Kennedy |
| 2006/0224226 A1 | 10/2006 | Huang et al. |
| 2007/0135898 A1* | 6/2007 | Burgermeister et al. .... 623/1.16 |
| 2007/0253996 A1 | 11/2007 | Bin et al. |
| 2007/0282433 A1 | 12/2007 | Limon et al. |
| 2007/0283552 A1* | 12/2007 | Gale et al. ....................... 29/515 |
| 2007/0290412 A1 | 12/2007 | Capek et al. |
| 2007/0293938 A1 | 12/2007 | Gale et al. |
| 2008/0001333 A1 | 1/2008 | Kleine et al. |
| 2008/0147164 A1* | 6/2008 | Gale et al. .................... 623/1.15 |
| 2008/0275537 A1* | 11/2008 | Limon ......................... 623/1.15 |
| 2009/0001633 A1 | 1/2009 | Limon et al. |
| 2009/0005860 A1 | 1/2009 | Huang et al. |
| 2009/0012598 A1 | 1/2009 | Abbate et al. |
| 2009/0146348 A1 | 6/2009 | Huang et al. |
| 2009/0319036 A1* | 12/2009 | Wang et al. .................. 623/1.49 |
| 2011/0066222 A1* | 3/2011 | Wang et al. .................. 623/1.15 |

FOREIGN PATENT DOCUMENTS

| | | |
|---|---|---|
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 03/034940 | 5/2003 |
| WO | WO 2004/067262 | 8/2004 |
| WO | WO 2006/014747 | 2/2006 |
| WO | WO 2007/142736 | 12/2007 |
| WO | WO 2007/146354 | 12/2007 |

OTHER PUBLICATIONS

Search Report for PCT/US2006/026455 filed Jul. 3, 2006, mailed Oct. 19, 2006 11 pgs.

Answers.com blow molding; retrieved from www.answers.com/blow%20molding#Stretch_blow_molding, Jun. 26, 2009, 11 pgs.

www.engineeringtoolbox.com/thermal/conductivity/d_429.html., Jun. 26, 2006, 4 pgs.

Herbert et al., "Characterizing the mechanical behavior of PLLA through Instrumented Indentation Testing", Agilent Technologies, Inc. 13 pgs. (2008).

Invitation to Pay Additional Fees for PCT/US2010/048287, mailed Mar. 7, 2011, 5 pgs.

* cited by examiner

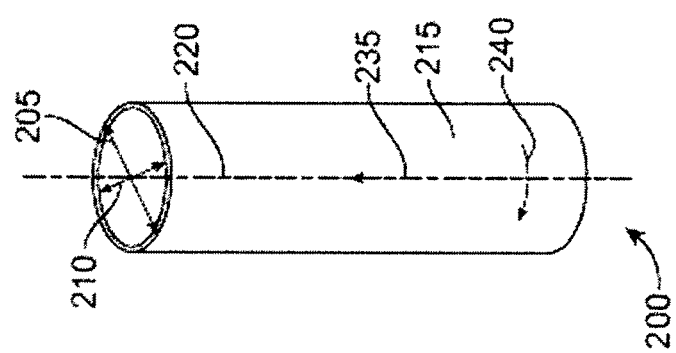

CONTROLLING CRYSTALLINE MORPHOLOGY OF A BIOABSORBABLE STENT

BACKGROUND OF THE INVENTION

1. Field of the Invention

This invention relates to methods of making a stent including deforming polymeric tubing precursor.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

A stent can be made in whole or in part of a biodegradable polymer. A biodegradable stent can be configured erode away from an implant site when it is no longer needed. A biodegradable stent allows further surgery or intervention, if necessary, on a treated vessel and reduces the likelihood of late stent thrombosis, a condition in which clots form on the surface of the stent months or years after deployment.

There are several characteristics that are critical stents, including high radial strength and high fracture toughness. Semi-crystalline polymer constructs from which stents are made require processing to improve these properties in order to obtain desired stent performance.

SUMMARY OF THE INVENTION

Various embodiments of the present invention include a method for fabricating stent comprising: radially expanding a PLLA tube; axially elongating the PLLA tube during the radial expansion, wherein the percent radial expansion is 300-500% and the percent axial elongation is 100-200%; and forming a stent pattern in the axially expanded and radially deformed tube.

Further embodiments of the present invention include a method for fabricating stent comprising: providing a PLLA tube disposed within a cylindrical mold; heating the mold and the tube to a tube deformation temperature with a heat source translating along the cylindrical axis of the mold and tube; increasing a pressure inside the tube; allowing the increased pressure in the tube to radially expand the tube against the inner surface of the mold, wherein the radial expansion propagates along the cylindrical axis of the mold and tube as the heat source heats translates along the cylindrical axis, applying a tensile force to the tube along the cylindrical axis during the radial expansion to axially elongate the tube during the radial expansion, wherein the percent radial expansion is 300-500% and the percent axial elongation is 100-200%; and forming a stent pattern in the axially expanded and radially deformed tube.

Additional embodiments of the present invention include a method for fabricating stent comprising: providing a PLLA tube disposed within a cylindrical mold; heating the mold and the tube to a tube deformation temperature with a heat source heating the entire mold and tube and once; increasing a pressure inside the tube; allowing the increased pressure in the tube to radially expand the tube against the inner surface of the mold, and subsequently cooling the entire mold and tube at once with a cooling source.

BRIEF DESCRIPTION OF THE DRAWINGS

FIG. 2 depicts a tube.

DETAILED DESCRIPTION OF THE INVENTION

Figure 1:
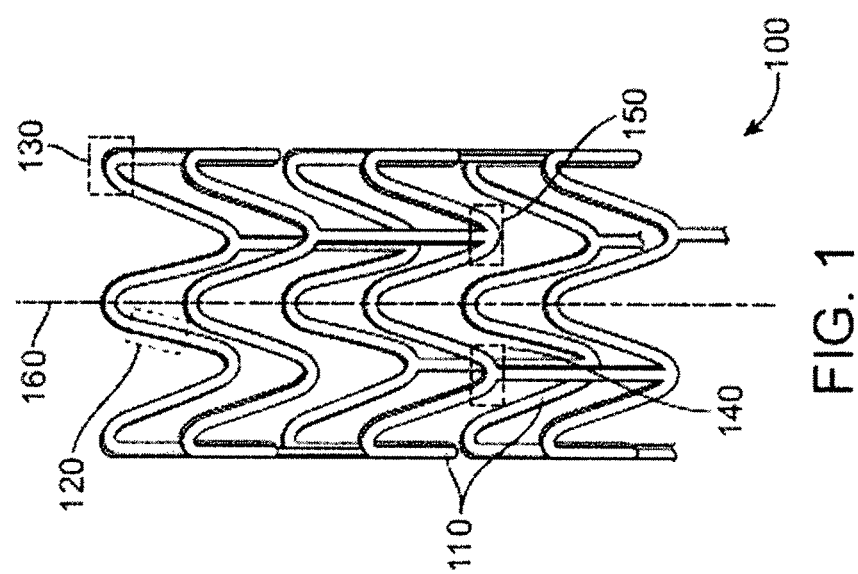
FIG. 1 depicts an exemplary stent.

The present invention can be applied to devices including, but is not limited to, self-expandable stents, balloon-expandable stents, stent-grafts, grafts (e.g., aortic grafts), and generally tubular medical devices. A stent can have a scaffolding or a substrate that includes a pattern of a plurality of interconnecting structural elements or struts. FIG. 1 depicts an example of a view of a stent 100. Stent 100 has a cylindrical shape with an axis 160 and includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1. The variation in stent patterns is virtually unlimited.

The underlying structure or substrate of a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

A stent such as stent 100 may be fabricated from a polymeric tube or a sheet by rolling and bonding the sheet to form a tube. For example, FIG. 2 depicts a tube 200. Tube 200 is cylindrically-shaped with an outside diameter 205 and an inside diameter 210. FIG. 2 also depicts an outside surface 215 and a cylindrical axis 220 of tube 200. In some embodiments, the diameter of the polymer tube prior to fabrication of stent may be between about 0.2 mm and about 5.0 mm, or more narrowly between about 1 mm and about 4 mm. Polymeric tubes may be formed by various types of methods, including, but not limited to extrusion or injection molding.

A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

Bending elements in a stent pattern bend inward when a stent is crimped to allow radial compression. Bending elements also bend outward when a stent is expanded to allow for radial expansion. After deployment, a stent is under static and cyclic compressive loads from the vessel walls. Thus, bending elements are subjected to deformation during use. "Use" includes, but is not limited to, manufacturing, assembling (e.g., crimping stent on a catheter), delivery of stent into and through a bodily lumen to a treatment site, and deployment of stent at a treatment site, and treatment after deployment.

Additionally, stent 100 is subjected to flexure along axis 160 when it is maneuvered through a tortuous vascular path during delivery. Stent 100 is also subjected to flexure when it has to conform to a deployment site that may not be linear.

Several mechanical properties or outputs are important for satisfactory stent performance during use. These include high radial strength, adequate toughness, minimal recoil, and resistance to physical aging. A stent scaffolding must have adequate strength, particularly, in the radial direction to withstand structural loads, namely radial compressive forces, imposed on the stent as it supports the walls of a vessel. Additionally, a stent must possess sufficient fracture toughness to resist cracking, fracture and premature failure from crimping, deployment, and lumen wall support. A stent should have sufficient toughness to resist to crack formation, particularly, in high strain regions. Recoil refers to the movement of a stent radially inward from its deployed diameter.

Some crystalline or semi-crystalline biodegradable polymers that are glassy or have a glass transition temperature (Tg) above body temperature are particularly attractive as stent materials due to their strength and stiffness at physiological conditions. Such glassy polymers can be absorbed through chemical degradation, such as hydrolysis. Physiological conditions refer to conditions that an implant is exposed to within a human body. Physiological conditions include, but are limited to, human body temperature, approximately 37° C.

Certain biodegradable polymers, such as poly(L-lactide) (PLLA), poly(glycolide) (PGA), and poly(L-lactide-co-glycolide) (PLGA), are attractive for use as stent scaffolding materials. This is in part due to their high strength and stiffness at physiological conditions. However, in the absence further processing, these polymers do not have adequate strength and fracture toughness for satisfactory performance of a stent with sufficiently thin struts, e.g., a width and thickness between 140-160 microns. The struts of a stent would have to be much larger than this to have radial strength sufficient to support the walls of a vessel. Additionally, these polymers exhibit a brittle fracture mechanism at physiological conditions. A stent fabricated from such polymers can have insufficient toughness for the range of use of a stent. As a result, cracks, particularly in high strain regions, can be induced which can result in mechanical failure of the stent.

There are various performance characteristics or outputs of a stent that are related to the strength and fracture toughness of a polymer material. These include the radial strength, recoil, the diameter at which the struts fracture upon deployment, and frequency of cracks. Various embodiments of the present invention includes processing a polymer tube, that is a precursor to a stent, to improve stent performance. The processing includes both radially expanding and axial elongating the polymer tube stent precursor. The radial expansion/axial elongation process results in the modification of the crystalline morphology of the polymer of the stent precursor which is believed to provide improved stent performance of a stent made from the precursor.

The degree of radial expansion of a tube can be quantified by a radial expansion (RE) ratio:

$$\frac{\text{Inside Diameter of Expanded Tube}}{\text{Original Inside Diameter of Tube}}$$

The RE ratio can also be expressed as a percent expansion: % Radial expansion (% RE)=(RE ratio−1)×100%.

Similarly, the degree of axial elongation, may be quantified by an axial elongation (AE) ratio:

$$\frac{\text{Length of Elongated Tube}}{\text{Original Length of Tube}}$$

The AE ratio can also be expressed as a percent expansion: % Axial expansion (% AE)=(AE ratio−1)×100%

Morphology includes, but is not limited to, degree of crystallinity, molecular orientation of polymer chains, and crystallite size. Molecular orientation refers to the relative orientation of polymer chains along a longitudinal or covalent axis of the polymer chains. The orientation can refer to the orientation of crystalline lamella and to the orientation polymer chains in the amorphous regions.

The strength and fracture toughness of a semicrystalline polymer material depend on or are influenced by the morphology since a semicrystalline polymer includes crystalline regions separated or surrounded by amorphous regions. The molecular orientation affects the strength the polymer material. Deforming a polymer induces a preferred orientation along the axis of deformation of the deformed polymer which increases the strength and modulus along this axis. The strength and modulus of a polymer generally increases as the degree of crystallinity increases, however, if it is too high, the polymer becomes brittle and susceptible to fracture. Additionally, it is believed that the smaller the size of the crystalline regions or domains, the greater the fracture toughness of the polymer.

Furthermore, the process is performed in a manner that maximizes the dimensional stability of the expanded and axially elongated tube. Dimensional stability refers the thickness of the tube walls and tubular shape. Also, it has been discovered that the homogeneity of the expanded and elongated tube are particularly sensitive to process parameters, which are adjusted to increase homogeneity.

The radial expansion/axial elongation process provides biaxial orientation around the circumference of the tube and along the cylindrical axis of the tube. The process also increases the crystallinity of the tube. In addition, the radial expansion/axial elongation process is performed at a temperature that favors nucleation over crystallite growth to provide small, dispersed crystals. Tubes and stents made therefrom made with different % RE, % AE, and different temperatures and other processing conditions will have different morphologies and properties.

As indicated above, deformation is known to increase strength along an axis of deformation. However, the dependence of stent performance on radial expansion and axial elongation of stent precursors is not discernable from this knowledge. The relationship between stent performance and the degree of expansion, the degree of axial elongation, and the ratio of the two is not understood. This may be due in part to the fact that the deformation and strain behavior of a stent pattern is more complex than that of a polymer tube. The stent deforms through bending at high strain regions. The stress and strain are not aligned along one direction, but follow the curvature the bending element. Additionally, the strain in these high strain regions varies as a function of the width of the bending region, being zero at the neutral axis.

The stent precursor polymeric tube is radially expanded and axially elongated by increasing the pressure inside the tube and applying a tensile force along the cylindrical axis of the tube, respectively. The pressure inside of the tube is increased by conveying a fluid into the tube to increase the internal pressure in the tube. Preferably, the tensile force is applied at one end while holding the other end stationary. Alternatively, a tensile force may be applied at both ends of the tube. The tube is preferably axially elongated during the radial expansion since this provides good dimensional stability. The tube can be axially elongated before or after radial expansion, however, this can result in poor dimensional stability such as on uniform wall thickness and departures from a cylindrical shape.

The tube is heated to a temperature between the glass transition temperature (Tg) and the melting temperature (Tm) of the polymer to allow the radial expansion and axial elongation of the tube.

At the start of the process, the tube is positioned in a cylindrical member or mold. The process parameters are adjusted so that the tube expands against the inside surface of the mold so that the outer diameter of the expanded tube is the inside diameter of the mold. One end of the tube is sealed or blocked and a gas such as air, nitrogen, oxygen, argon, etc. is conveyed in the other end of the polymer tube to increase the pressure in the tube.

The tube is heated by a heating source such as a nozzle or nozzles blowing a warm gas onto a portion of the tube. The nozzle(s) are translated along the cylindrical axis of a the tube from a proximal end to a distal end, blowing warm gas onto an axial section or portion of the mold as it translates which heats the axial section or portion of the mold and the axial section or portion of the tube within the mold. The temperature and nozzle rate are adjusted so that as the nozzles translates, the heated portion expands. The radial expansion follows the translating nozzle and propagates along the cylindrical axis of the tube. As the nozzle translates, the an end of the tube is pulled at a specified rate, which is preferably constant.

In another embodiment, a nozzle with an fluid outlet that extends along the length can heat the entire length of the tube at the same time. In this embodiment, the nozzle does not translate. Once expanded, the same or similar nozzle is employed to cool the entire length of the tube at the same time. In this fashion, heating and cooling rates of the entire tube can be controlled and done at once.

The nozzle rate and pull rate are preferably adjusted so that expansion and axial elongation start at the same time and are completed at the same time. Alternatively, the nozzle rate and pull rate can be adjusted so that either the expansion or elongation is completed first, however, this may lead to poor dimensional stability and nonuniform thickness and shape.

Additionally, this may lead to axial nonuniformity in elongation along the axis of the tube. The reason for this is that the portion of the tube under the nozzle will likely experience the greatest elongation at any given time since it is at the deformation temperature. Therefore, starting or stopping elongation at times different from radial expansion will likely lead to different degrees of elongation in different axial sections of the tube. Since the elongation modifies morphology and properties, the tube and stent formed therefrom will have different properties along the axis of the tube and stent.

Additionally, the nozzle rate and pull rate are preferably constant since the properties of a deformed polymer generally depend on the rate of deformation. A variable radial expansion and elongation rate in different parts of the tube could lead to different properties along the length of a deformed tube.

Preferably, prior to the expansion and elongation, the tube is pre-heated close to a temperature close to (e.g., within 5-10° C. of the deformation temperature) or at the deformation temperature. Pre-heating can be performed by nozzle can be translated along the length of the tube without the increased pressure and the tension.

Once the expansion and elongation are completed for a tube, the tube can optionally be annealed to enhance dimensional stability. In the annealing, the pressure and the tension can be maintained while the temperature of the tube is maintained between Tg and Tm. Generally, when a semicrystalline polymer is maintained in this temperature range, the crystallinity increases. However, the inventors have found that for PLLA the crystallinity does not increase or significantly increase after the deformation process is completed.

After the expansion and elongation is completed, the polymer tube is cooled or allowed to cool to below its Tg either before or after decreasing the pressure and/or decreasing tension. Cooling the tube helps insure that the tube maintains the proper shape, size, and length following its formation. Upon cooling, the deformed tube retains the length and shape imposed by an inner surface of the mold in the absence of a pressure above ambient or atmospheric pressure.

A extruded polymer tube for use in manufacturing a stent can have a diameter of 2-4 mm. However, the present invention is applicable to polymer tubes less than 1 mm or greater than 4 mm. The wall thickness of the polymer tube can be 0.03-0.06 mm, however, the present invention is application to tubes with a wall thickness less than 0.03 mm and greater than 0.06 mm.

Figure 3A:
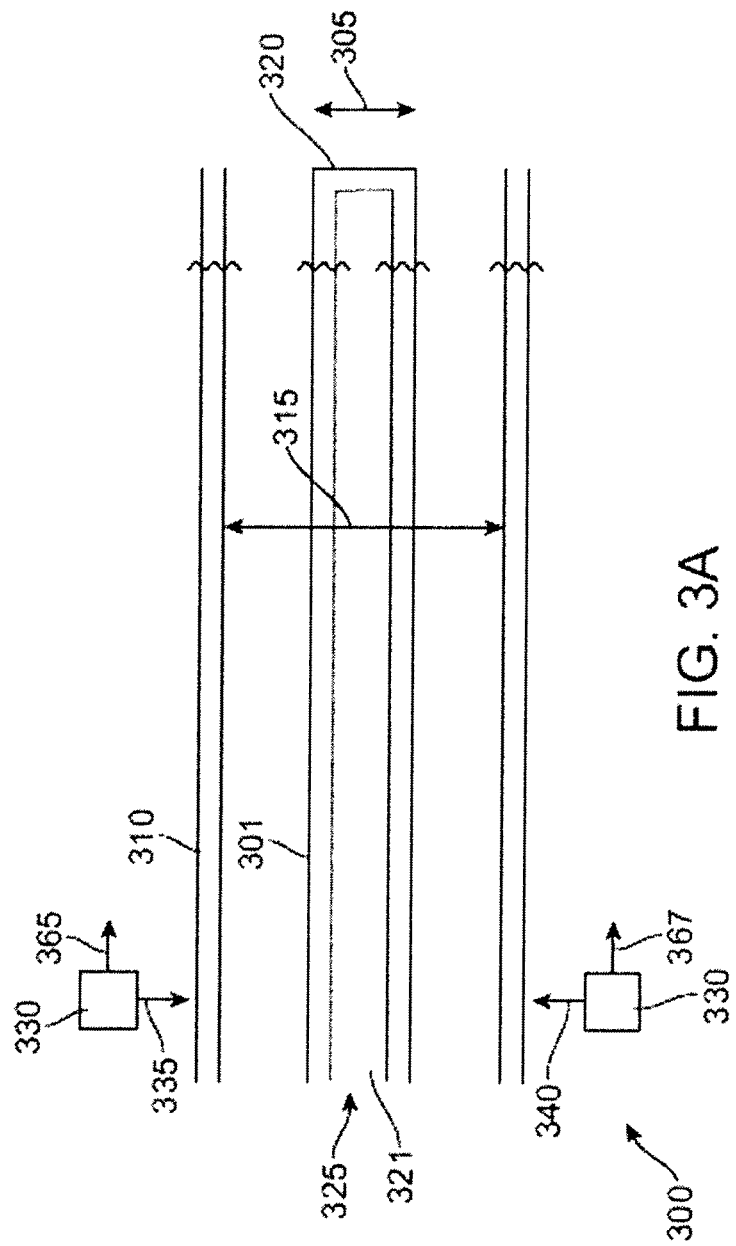
FIGS. 3A-3C depict radially expansion and axially elongation a polymeric tube.
Figure 3B:
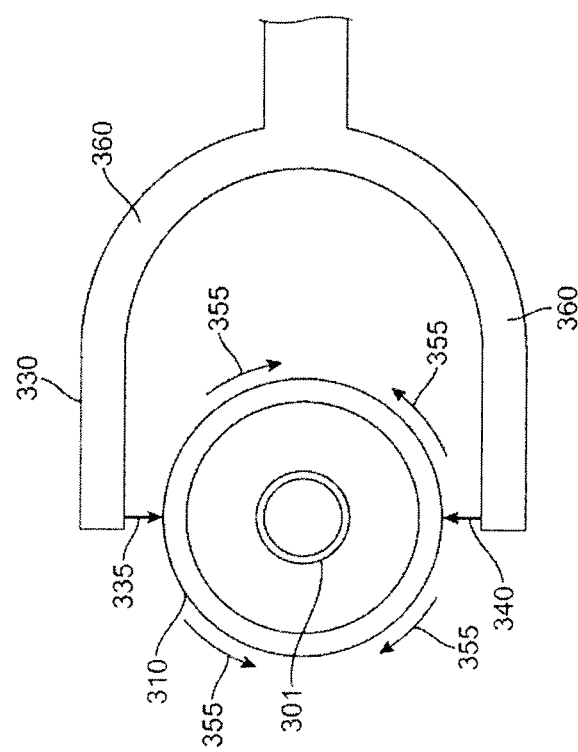
Figure 3C:
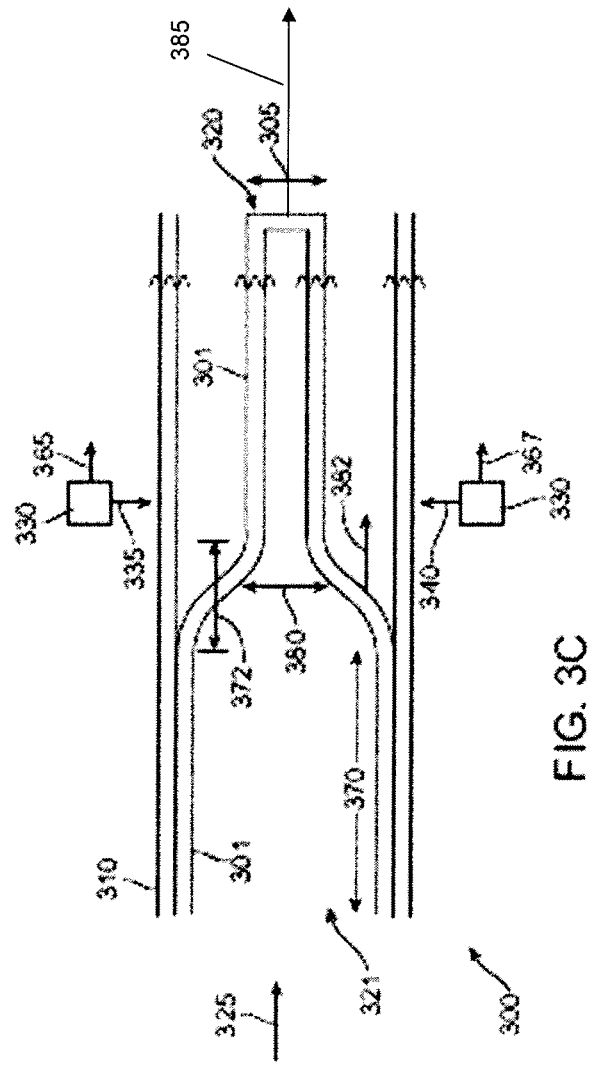

FIGS. 3A-C depict a system 300 which illustrates in detail the radial expansion and axial elongation process. FIG. 3A depicts an axial cross-section of a polymer tube 301, prior to expansion and elongation, with an outside diameter 305 positioned within a mold 310. The process parameters are adjusted so that polymer tube 301 expands onto and is molded by the inside surface of mold 310. Polymer tube 301 has an outside diameter 315 in its expanded state which is the inside diameter of mold 310. Polymer tube 301 is closed at a distal end 320. Distal end 320 may be open in subsequent manufacturing steps.

A gas is conveyed, as indicated by an arrow 325, into an open proximal end 321 of polymer tube 301 to increase an internal pressure within tube 301 to radially deform tube 301. A tensile force is applied at distal end 320 in the form of a constant pull rate, as shown by an arrow 385 in FIG. 3C.

Polymer tube 301 is heated by a nozzle 330 with fluid ports that direct a heated gas at two circumferential locations of mold 310 to heat an axial portion of tube 310, as shown by arrows 335 and 340. FIG. 3B depicts a radial cross-section showing tube 301, mold 310, and nozzle 330 having structural members 360. Additional fluid ports can be positioned at other circumferential locations of the axial portion of mold 310. The heated fluid flows around mold 301, as shown by arrows 355, to heat mold 310 and tube 301 to a temperature above the Tg of the polymer of tube 301.

Nozzle 330 translates along the longitudinal axis of tube 301 as shown by arrows 365 and 367. As nozzle 330 translates along the axis of mold 310, the axial portion of tube 301 adjacent to the nozzle radially expands. The temperature and pressure are high enough and the nozzle translation rate is slow enough so that the radially expanded portion expands against the inner surface of mold 310. The radial expansion follows the translation of nozzle 330. The heated portion of tube 301 radially expands due to the increased temperature of tube 301 and the increased pressure, as depicted in FIG. 3C.

Referring to FIG. 3C, an expanding section 372 and an expanded section 370 of tube 301 are shown. Section 372 deforms radially as shown by an arrow 380. Deformed section 370 has an outside diameter the same as the outside diameter of mold 310. The deformation in the radial direction is shown by arrow 380 in FIG. 3C and the axial component is shown by an arrow 382 in FIG. 3C.

Processing parameters of the above-described process include, but are not limited to, the temperature and pressure at which the tube expands, the nozzle translation rate, and pull rate. The process parameters for a specified % RE and % AE are selected based on several factors.

As indicated above, smaller crystallite size is likely to enhance fracture toughness. Under quiescent conditions or quiescent crystallization, the nucleation rate is much is much higher at lower temperatures close to Tg. Quiescent crystallization is crystallization of a polymer that is not under any external stress that would strain the polymer. This is also expected to be the case for strain-induced crystallization which occurs over a much smaller time scale during the tube deformation process. Therefore, the deformation temperature is chosen to be as low as possible or as close a possible to Tg.

However, the inventors have found there are factors place an lower limit on the temperature. The temperature must be high enough so that the heated portion expands to contact the mold inner surface. Also, the temperature must be high enough so that the portion under the nozzle expands as the nozzle translates. Another factor is that if the temperature is too low, the expanded tube can have a cloudy appearance. The temperature should be high enough so that that expanded tube has a clear appearance.

Another limitation on process parameters, observed by the inventors, is that the homogeneity of expanded/elongated tube depends on the deformation temperature. Such homogeneity is critical for stent performance. Properties such as modulus of elasticity and hardness vary as a function of depth from the inside and outside surface of deformed tubes. At lower temperatures, there is a disparity in the hardness as a function of depth between the inside and outside surfaces. There is also a disparity in the modulus of elasticity as a function of depth between the inside and outside surfaces. This disparity is reduced or eliminated as the deformation temperature is increased. This was demonstrated by nanoindentation measurements of the modulus of elasticity and hardness as a function of depth for expanded/elongated PLLA tubes. In some embodiments, to address this issue, a deformation temperature is adjusted for a given % RE/% AE, to a temperature at which the disparity between the properties is reduced or eliminated. The other processing parameters are adjusted accordingly to compensate for the increase in temperature.

The tube can be preheated for between 4-32 s to the deformation temperature. The inventors have found that for a PLLA tube, a temperature of at least about 10-20° C. or 20-40° C. above the Tg of the tube polymer is preferred. In particular, the deformation temperature of a PLLA tube can be 70-75° C., 75-80° C., 85-90° C., 95-100° C., 100-105° C., 105-110° C., 115-120° C., and 125-130° C.

The expansion pressure is bounded from below by a minimum pressure required to expand the tube to the wall of the mold and from above by a pressure that would tear the tube. The pressure can be 90-160 psi, or more narrowly 110-140 psi.

The nozzle translation rate is adjusted to be slow enough to allow the tube to be sufficiently heated to expand. The nozzle translation rate can be 0.2-1.2 mm/s, or more narrowly 0.32-1.0 mm/s.

The pull rate is adjusted so tube length reaches the specified % AE at or before the expansion is completed, but not large enough to break or tear tube. The pull rate can be 0.4-4.0 mm/s, or more narrowly 0.58-3.8 mm/s.

Additionally, the inventors have found the there is an upper limit to the crystallinity that can be obtained from strain-induced crystallization that occurs as a result of the radial expansion and axial elongation. This upper limit is lower that is obtained from quiescent crystallization. The upper limit of crystallinity of a PLLA tube is between 45-50%. A crystallinity much above 50% would make the stent too brittle.

Both increase in crystallinity and radial expansion/axial elongation are important for improvement of stent properties. Therefore, it is important to obtain both at the same time, as in the present invention, for better control crystallinity and deformation. As indicated herein, quiescent crystallization can results in a much higher and possible undesirable crystallinity. It is also important for the deformation to be performed in the temperature range that crystallinity can increase, i.e., between Tg and Tm.

The inventors have found that the strength and fracture toughness of an expand/elongated tube and the stent performance vary with or depend the degree of radial expansion (RE) and axial elongation (AE) and their ratio. The % RE can be less than 100%, 100-200%, 200-300%, 300-400%, 400-500%, or greater than 500%. The % AE can be less than 20%, 20-50%, 50-100%, 100-150%, 150-200%, or greater than 200%. A deformed tube can have any combination of the % RE and % AE of the above ranges. For example, for a % RE of 400-500% the % AE can be less than 20%, 20-50%, 50-100%, 100-150%, 150-200%, or greater than 200%. For example, for a % RE of 300-400% the % AE can be less than 20%, 20-50%, 50-100%, 100-150%, 150-200%, or greater than 200%. For example, for a % RE of 200-300% the % AE can be less than 20%, 20-50%, 50-100%, 100-150%, 150-200%, or greater than 200%. For example, for a % RE of 100-200% the % AE can be less than 20%, 20-50%, 50-100%, 100-150%, 150-200%, or greater than 200%. In this application, all endpoints of ranges are included in any designated ranges.

For PLLA stent made according the methods described herein, the inventors observed particularly favorable results for radial strength and deployment to fracture for combinations with % RE of 300-500% and % AE of 100-200% greater.

A stent made from a radially expanded tube with no or a relatively small amount of axial elongation can cause an imbalance in mechanical properties along radial and axial directions. Pre-clinical data have shown that this can result in weak areas in the stent structure where a stronger axial strength component is important. The inventors have shown with a PLLA tube and stent experiments that the improvement of stent performance due higher axial elongation over a stent with lower axial elongation.

The stent outputs considered in this application include radial strength, recoil, the diameter at which the struts fracture upon deployment, and frequency of cracks. These outputs are related generally to the strength and fracture toughness of the tube. Although the trend or dependence of these stent outputs on % RE and % AE is not discernible from this knowledge, there are several reasonable propositions.

The stent performance may be optimal with % RE/% AE ratio close to one since this represents a balance of the induced strength. However, due to the complexity of the design and how it affects mechanical properties during crimping and expansion, a % RE/% AE ratio where % RE dominates may be preferred. Additionally, stent performance may be expected to be correlated with the tube mechanical properties along the hoop and axial directions, such as the strength and elongation at break. In other words, stent performance may be correlated with the tube hoop and axial properties. The inventors have found unexpectedly that neither of these propositions is the case.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

For the purposes of the present invention, the following terms and definitions apply:

"Radial strength" of a stent is defined as the pressure at which a stent experiences irrecoverable deformation.

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that results from the applied force. For example, a material has both a tensile and a compressive modulus.

"Stress at peak" is the maximum tensile stress which a material will withstand prior to fracture. Stress at break can also be referred to as the tensile strength. The stress at break is calculated from the maximum load applied during a test divided by the original cross-sectional area.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Example 1

The following example describes the mechanical testing results of radially expanded and axially elongated PLLA stent tube precursors (deformed tubes) and stents made therefrom. A commercially available balloon blower or expander was modified and used for radially expanding and axially elongating the polymer tubes.

Properties of Tube

The tubes were made by extrusion of 100% PLLA resin. The diameter of the extruded tubes varied and depended on the degree of radial expansion. The final diameter of all the deformed tubes were the same and the corresponding stents made from the tubes have the same diameter. Therefore, an extruded tube for forming a deformed tube with 500% RE has a smaller diameter than the extruded tube for forming a deformed tube with 200% RE. The target diameter for the deformed tubes and stents made therefrom is 3 mm. The crystallinity of the extruded tubes was approximately 15-20% as measured by DSC at 20° C./minute.

Properties of Stent

Figure 4:
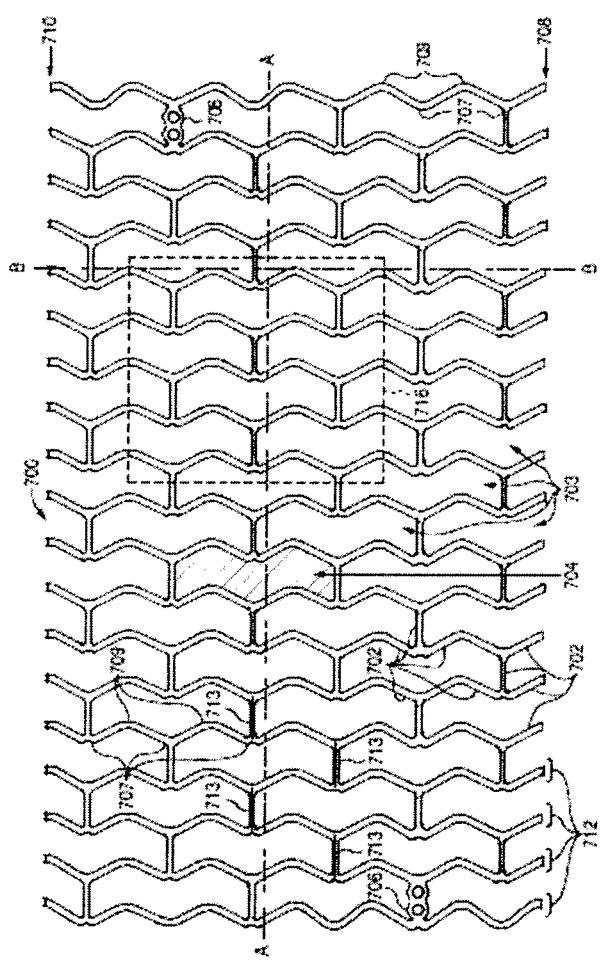
FIG. 4 shows the general structure of the stent pattern of the stents tested.

The stents were formed by forming a pattern in the deformed tubes using a 120 fs femtosecond laser. The width of the struts is about 150 microns. FIG. 4 shows the general structure of the stent pattern of the stents tested. Stent pattern 700 is shown in a flattened condition so the pattern can be clearly viewed. When the flattened portion of stent pattern 700 is in a cylindrical form, it forms a radially expandable stent. The stent pattern 700 includes various struts 702 oriented in different directions and gaps 703 between the struts. Each gap 703 and the struts 702 immediately surrounding the gap 703 defines a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. All the cells 704 have the same size and shape. Line A-A is parallel to the central axis of the stent. The pattern 700 is illustrated with a bottom edge 708 and a top edge 710. On a stent, the bottom edge 708 meets the top edge 710 so that line B-B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction. The angle at the crests or troughs is between 124-128°.

Still referring to FIG. 4, the rings 712 are connected to each other by linking struts 713 that are parallel to line A-A. The rings 712 are collapsed to a smaller diameter during crimping and expanded to their original diameter or to a larger diameter during deployment in a vessel.

Test Samples and Conditions

The different combinations of % RE and % AE and the corresponding deformation temperatures are provided in Table 1. For each % RE/% AE combination, tubes were made at two different deformation temperatures.

TABLE 1

Combinations % RE and % AE of PLLA tubes and expansion conditions.

| Radial | Axial | Temp (° C.) | Group Name |
|---|---|---|---|
| 500% | 20% | 96 | A |
|  |  | 106 | B |
|  | 100% | 104 | C |
|  |  | 114 | D |
|  | 200% | 110 | E |
|  |  | 120 | F |

TABLE 1-continued

Combinations % RE and % AE of PLLA tubes and expansion conditions.

| Radial | Axial | Temp (° C.) | Group Name |
|---|---|---|---|
| 400% | 20% | 74 | G |
|  |  | 84 | H |
|  | 100% | 102 | I |
|  |  | 112 | J |
|  | 200% | 110 | K |
|  |  | 120 | L |
| 300% | 33% | 77 | M |
|  |  | 87 | N |
|  | 100% | 74 | O |
|  |  | 84 | P |
|  | 200% | 96 | Q |
|  |  | 106 | R |
| 200% | 20% | 82 | S |
|  |  | 92 | T |
|  | 100% | 82 | U |
|  |  | 92 | V |
|  | 200% | 104 | W |
|  |  | 114 | X |

The other processing conditions for the Groups in Table run are:
Pressure—110-140 psi
Heat Nozzle Speed—0.32-1.0 mm/s
Pull Speed—0.58-3.8 mm/s
Pre-heat time (pre-heating occurs at the temperature for each Group)—4-32 s.

Six combinations of % RE/% AE in Table 1 were selected for mechanical property analysis of deformed tubes and stents. With the exception of Group G, 400/20, the tubes with the higher processing temperature were selected. The higher temperature was selected because the inventors observed better homogeneity in the deformed tubes at the higher temperature. The other five conditions selected were the Group B—maximum % RE, minimum % AE (500/20); Group F—maximum % RE, maximum % AE (500, 200); Group T—minimum % RE, minimum % AE (200, [20, 33, or 50]); Group X—minimum % RE, maximum % AE (200, 200); Group P—midpoint % RE, and midpoint % AE (300, 200). With respect to Group T, the % AE was adjusted to obtain a tube thickness within stent specifications.

The mechanical properties of the both the deformed tubes and the stents have been measured for each group. The following properties of the deformed tubes were measured:
The crystallinity was determined using differential scanning calorimetry (DSC).
The Tg or onset of glass transition was determined using differential scanning calorimetry (DSC).
The ultimate strength and the elongation at break were determined for the deformed tube in the hoop and the axial directions. Hoop properties were determined by cutting a hoop or ring off of the end of a deformed tube, cutting a notch in the tube, and pulling on the tube in opposite direction with pins inserted in the tube until the tube broke. The axial properties were determined by pulling on a tube along its cylindrical axis. The elongation at break is the amount of elongation that occurs from the point of yield to break.
The radial and axial modulus of the deformed tubes were measured with dynamical mechanical analysis (DMA).
The following properties were measured for the stents:
Radial strength and radial stiffness were measured with MSI RX650 radial expansion force gauge equipment made by Machine Solutions Inc. of Flagstaff, Ariz.
Recoil was measured with Nikon camera equipment.
The diameter at deployment to fracture was measured by first crimping the stent to 1.3 mm an then deploying the stent until a fractured (broken) strut was observed.
Crack counts at deployment of 3 mm was measured by first crimping the stent to 1.3 mm and then deploying to 3 mm. Crack counts were measured at 3.5 mm by deployment the same stent to 3.5 mm.

Figure 5:
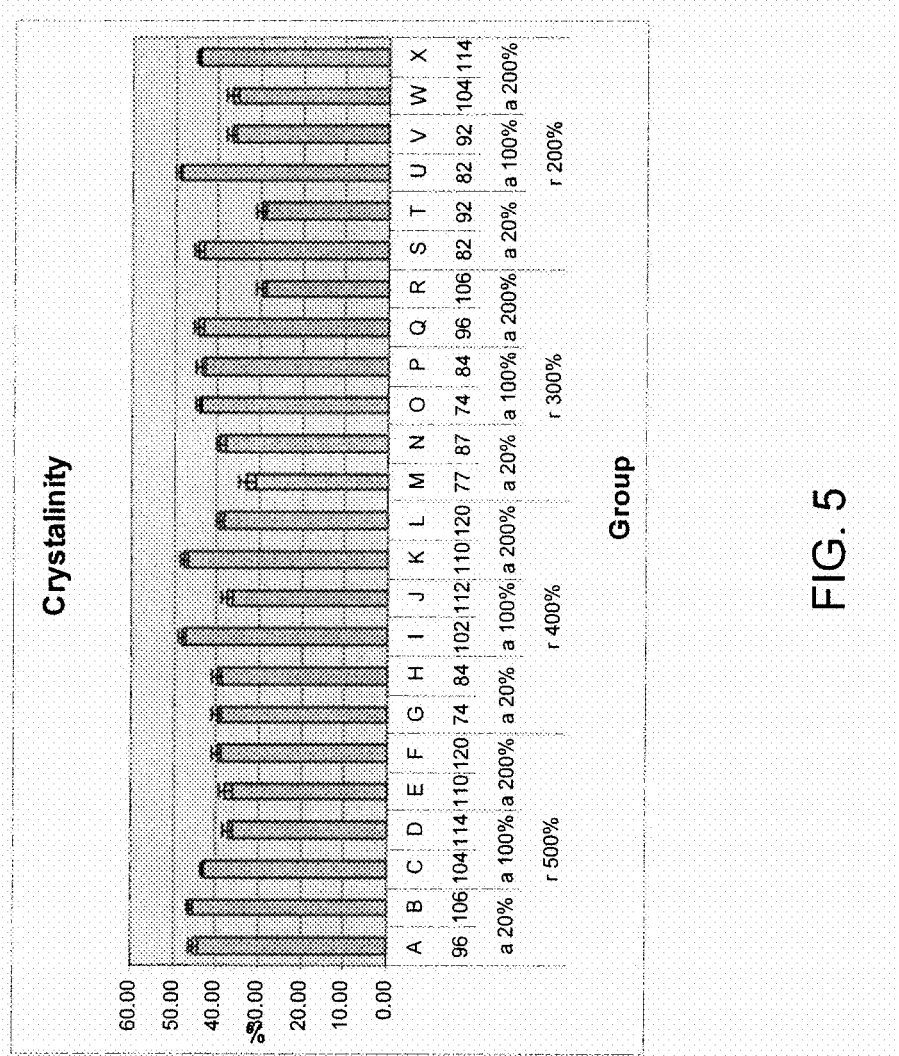
FIG. 5 depicts the crystallinity of deformed PLLA tubes as determined by DSC.

Properties of Deformed Tubes
Crystallinity of Deformed Tubes
FIG. 5 depicts the crystallinity of the deformed tubes as determined by DSC. The maximum crystallinity obtained was less 50%. A crystallinity up to 60% is possible. Based on a model fit of the data to the % RE and % AE, there was only a moderate correlation ($R^2=0.76$) between the crystallinity and the % RE and % AE.

Figure 6:
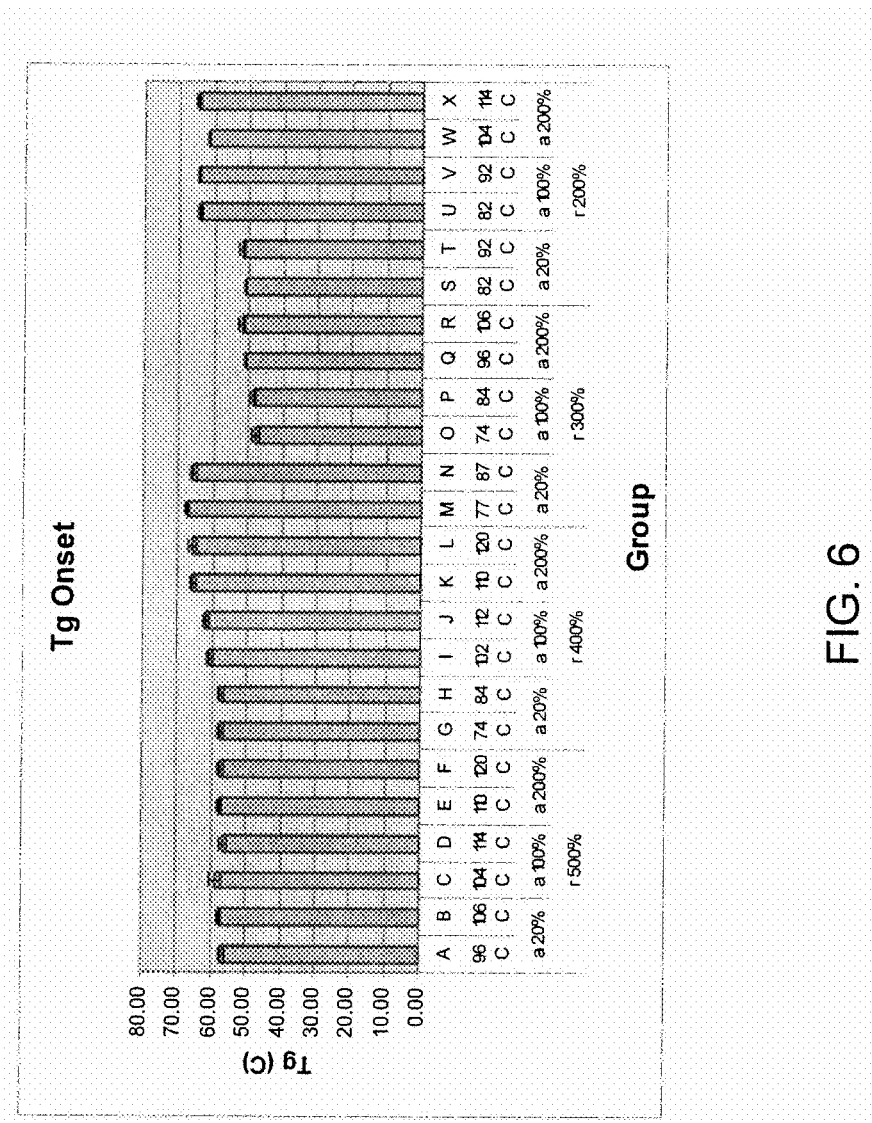
FIG. 6 depicts the Tg onset of deformed PLLA tubes as determined by DSC.

Tg Onset of Deformed Tubes
FIG. 6 depicts the Tg onset of the deformed tubes as determined by DSC. Based on a model fit of the data to the % RE and % AE, there was a weak correlation ($R^2=0.43$) between the Tg onset and the % RE and % AE.

Figure 7:
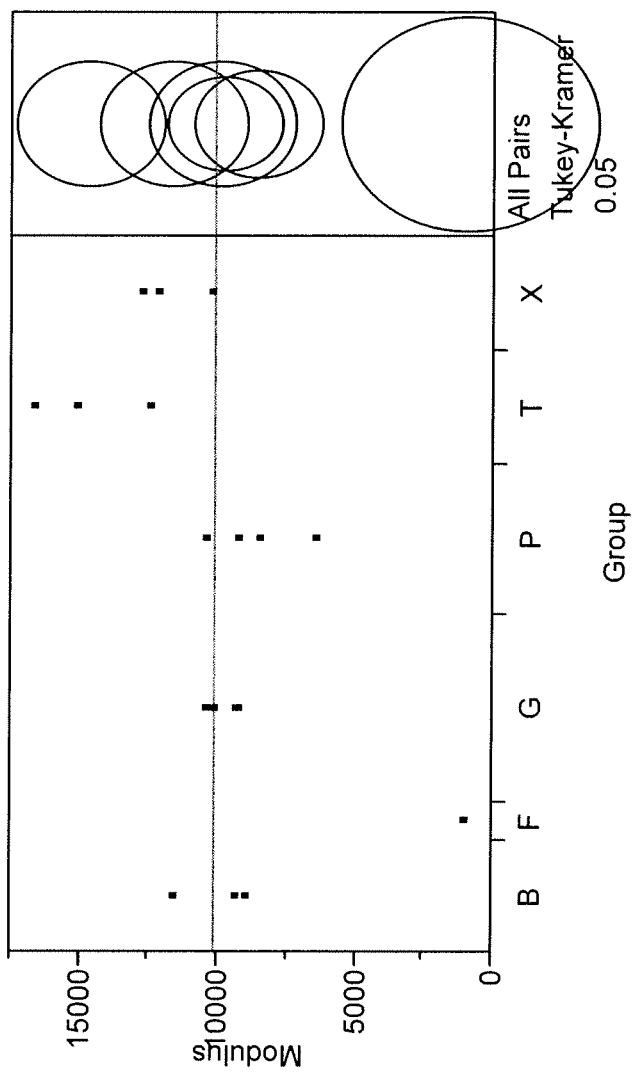
FIG. 7 depicts a plot of the modulus values for deformed PLLA tubes with different radial expansions and axial elongations.

DMA Analysis of Deformed Tubes
FIG. 7 depicts a plot of the modulus values for deformed tubes in Groups B, F, G, P, T, and X. The modulus values fell in to three groups: (1) T and X; (2) X, B, G, and P; and (3) F. No correlation was observed between the modulus and % RE and % AE.

Figure 8:
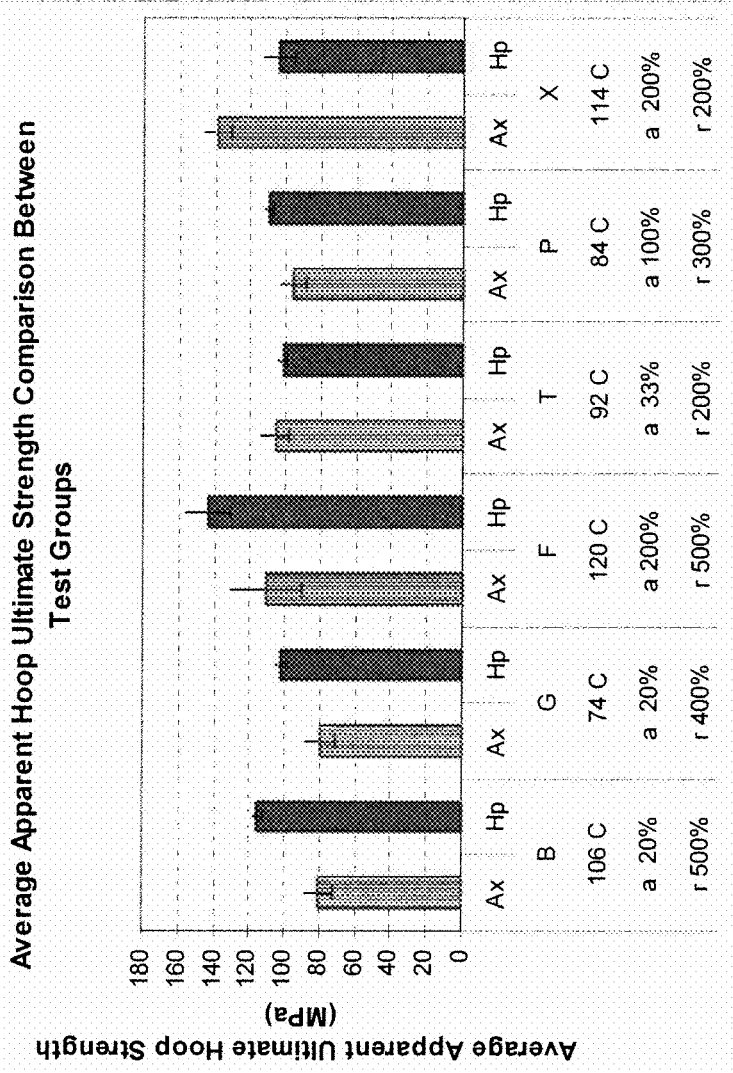
FIG. 8 depicts a bar chart with a comparison of the ultimate strength of deformed PLLA tubes with different radial expansions and axial elongations.

Ultimate Strength and the Elongation at Break
FIG. 8 depicts a bar chart with a comparison of the ultimate strength of deformed tubes in Groups B, G, F, T, P, and X. Group F, 500/200, has the highest hoop strength. Group X, 200/200 has the highest axial strength. Based on a model fit of the ultimate strength data to the % RE and % AE, there was a poor correlation ($R^2=0.42$) between the ultimate strength and the % RE and % AE.

The ultimate strength data demonstrates some synergy of the radial expansion/axial elongation. For example, Group B has the same RE (500%) and a lower AE (20%) compared to Group F. However, the larger % AE of Group F results in both a higher axial strength and hoop strength.

Figure 9:
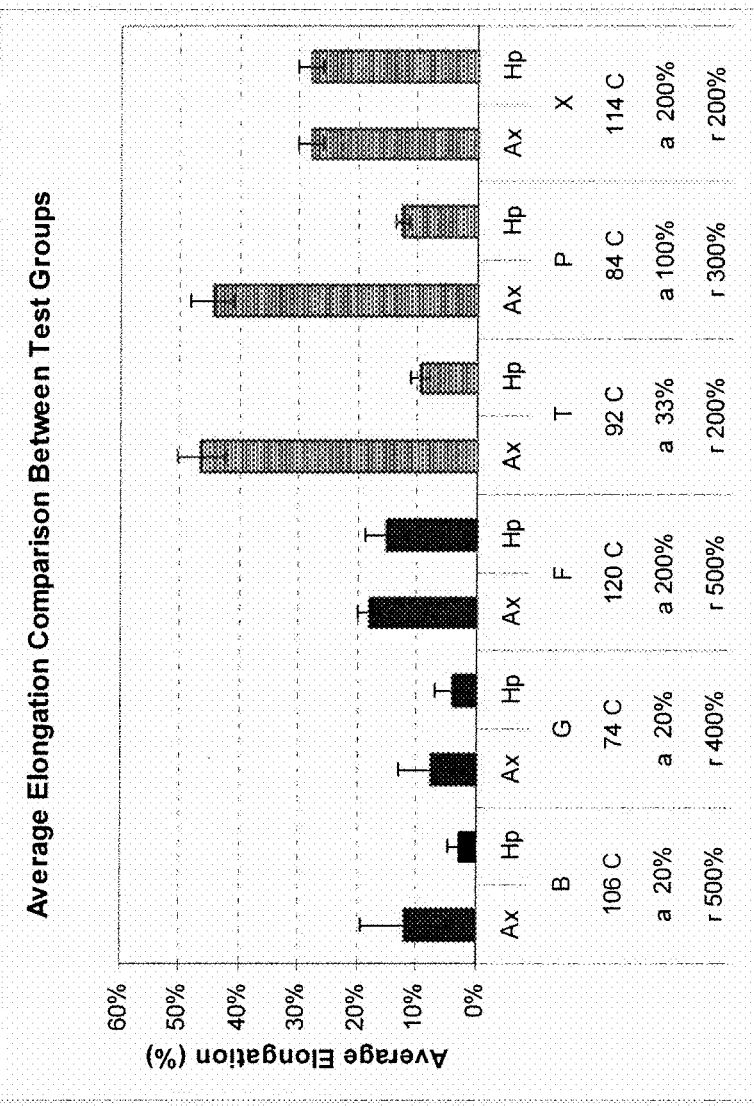
FIG. 9 depicts a bar chart with a comparison of the elongation at break of deformed PLLA tubes with different radial expansions and axial elongations.

FIG. 9 depicts a bar chart with a comparison of the elongation at break of deformed tubes in Groups B, G, F, T, P, and X. Groups T (200%/33%) and P (300%/100%) have the highest hoop elongation at break. Based on a model fit of the elongation data to the % RE and % AE, there was moderate correlation ($R^2=0.83$) between the elongation at break and the % RE and % AE.

The data demonstrates the some synergy of the radial expansion/axial elongation. For example, Group B has the same % RE (500%) and a lower % AE (20%) compared to Group F. However, the larger % AE of Group F results in both a higher axial elongation at break and hoop elongation at break.

Figure 10:
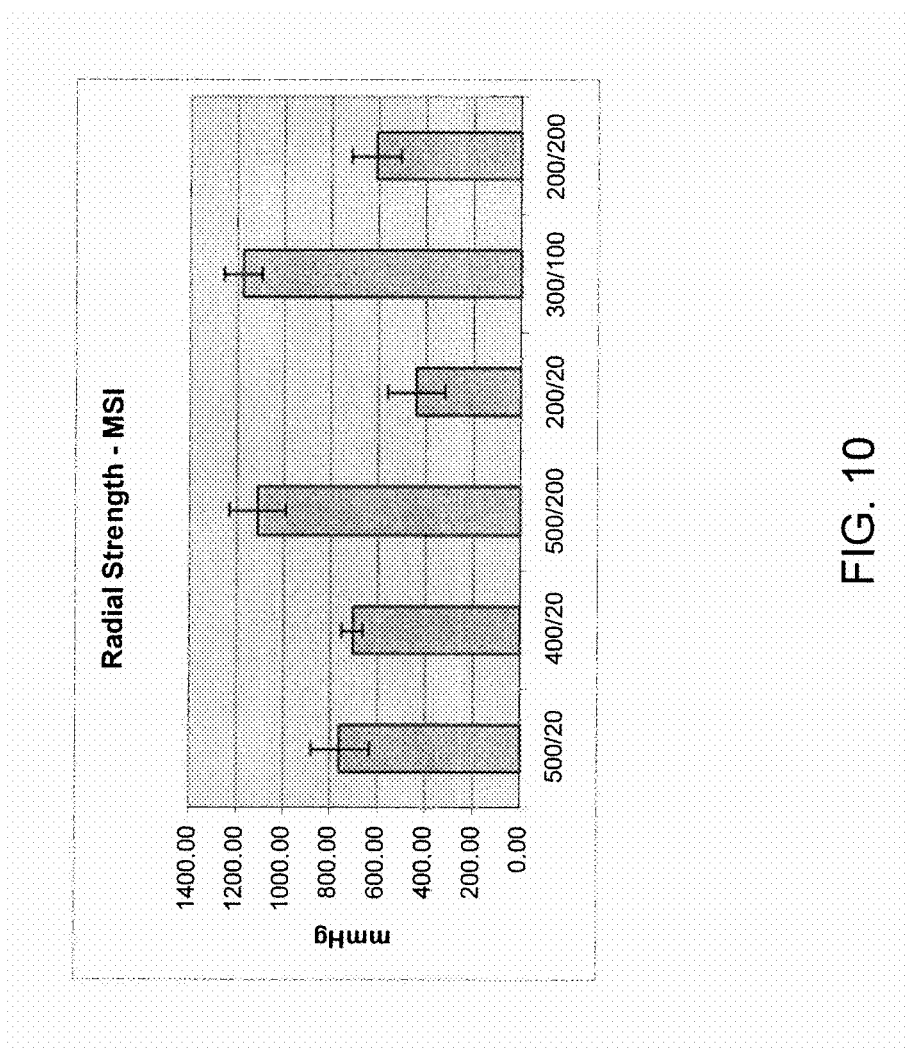
FIG. 10 depicts a bar chart with a comparison of the radial strength of stents made from PLLA tubes with different radial expansions and axial elongations.

Properties of Stents
Radial Strength of Stent
FIG. 10 depicts a bar chart with a comparison of the radial strength of stents made from tubes with % RE/% AE of 500/20 (Group B), 400/20 (Group G), 500/200 (Group F), 200/33 (Group T), 300/100 (Group P), and 200/20 (Group X). Based on a model fit of the radial strength data to the % RE and % AE, the was a good correlation ($R^2=0.89$) between the radial strength and the % RE and % AE. Radial strength increases with an increase in radial expansion and axial elongation.

Group P, 300/200 has the highest radial strength and Group F, 500/200 is the second highest, having a slightly lower value within the margin of error. The data demonstrates the synergy of the radial expansion/axial elongation. For example, Group B has the same % RE (500%) and a lower % AE (20%) compared to Group F. However, the larger % AE of Group F results in a higher radial strength.

In addition, there is an unexpected lack of correlation between the hoop strength of a deformed tube and the radial strength of the corresponding stent. For example, the Group F (500/200) deformed tube has the highest ultimate strength in the hoop direction, with the Group P (300/100) deformed tube having an ultimate strength well below the Group F tube. However, as stated above, the Group P stent has a radial strength above the Group F stent.

Deployment to Fracture

Figure 11:
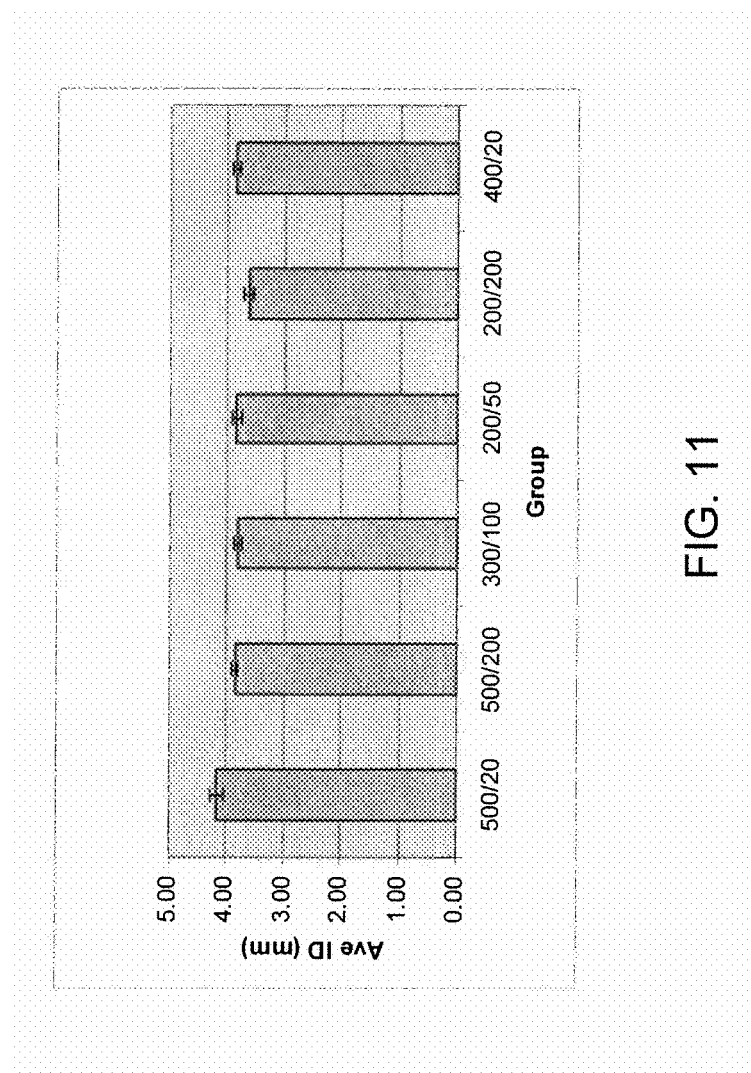
FIG. 11 depicts a bar chart with a comparison of the diameter at deployment to fracture of stents made from PLLA tubes with different radial expansions and axial elongations.

FIG. 11 depicts a bar chart with a comparison of the diameter at deployment to fracture of stents made from tubes with % RE/% AE of 500/20 (Group B), 400/20 (Group G), 500/200 (Group F), 200/33 (Group T), 300/100 (Group P), and 200/50 (Group X). The 500/20 stent has values statistically higher than 500/200, 300/100, 400/20, and 200/50. The 200/200 stent has a value statistically lower than the rest. The 500/200, 300/100, 400/20, and 200/50 are still within acceptable performance range. Based on a model fit of the diameter at deployment at break data to the % RE and % AE, there was a moderate correlation ($R^2=0.79$) between the radial strength and the % RE or % AE.

Predictions of % RE/% AE for Maximum Radial Strength and Deployment to Fracture

Figure 12A:
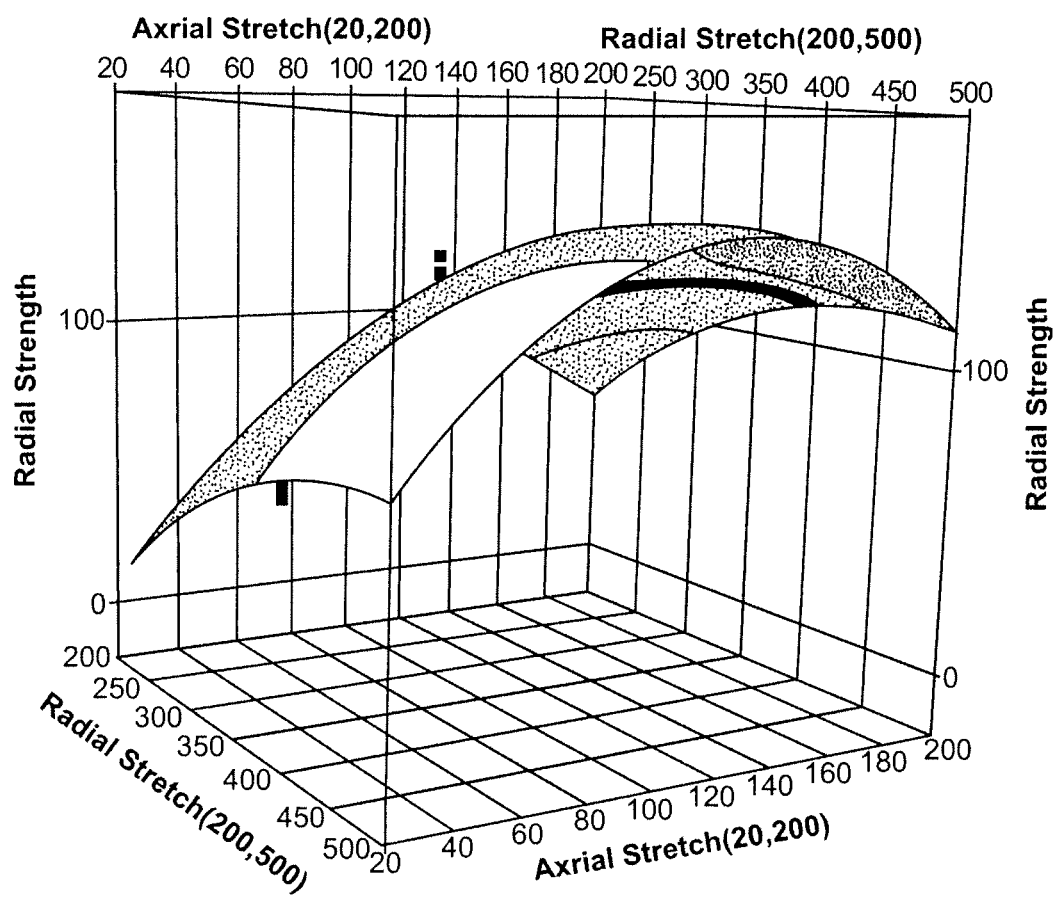
FIG. 12A depicts the radial strength of stents versus radial expansion and axial elongation.
Figure 12B:
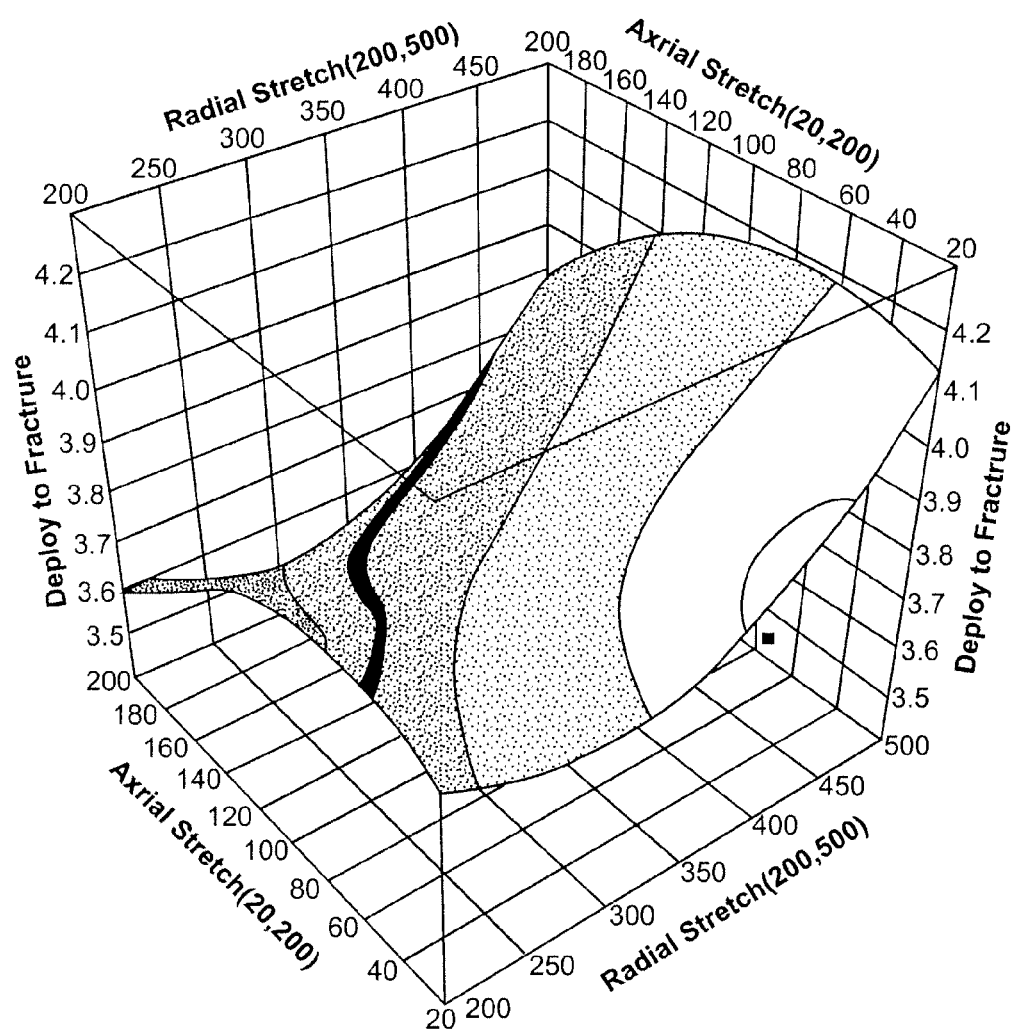
FIG. 12B depicts the diameter at deployment to fracture of stents versus radial expansion and axial elongation.

The predictive model generated from the radial strength data was used to predict the values of % RE and % AE that provide maximum radial strength. Likewise, the predictive model generated from the deployment to fracture data was used to predict the values of % RE and % AE that provide the maximum diameter of deployment to fracture. FIG. 12A depicts the radial strength versus % RE and % AE. As shown by the figure, the relationship is a downward facing concave surface which reaches a maximum % RE/% AE value and then curves downward at higher values of % RE/% AE. The maximum value of the radial strength occurs at 450/125% RE/% AE with the radial strength being 1462 mm Hg and a deployment to fracture of 4.0 mm. FIG. 12B depicts the diameter at deployment to fracture versus % RE and % AE. The maximum deployment to fracture occurs at 500/75% RE/% AE, with the radial strength being 1288 mm Hg and the deployment to fracture being 4.2 mm.

Crack Counts

Figure 13A:
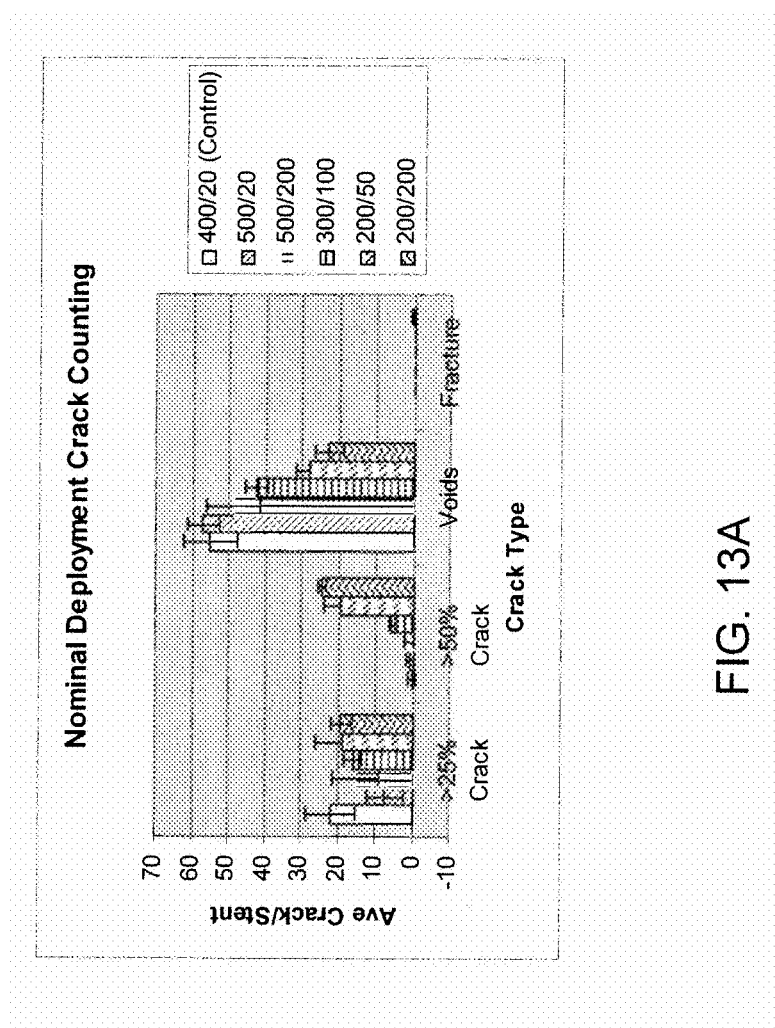
FIGS. 13A-B depict crack count results for stents at 3 mm and 3.5 mm deployment.
Figure 13B:
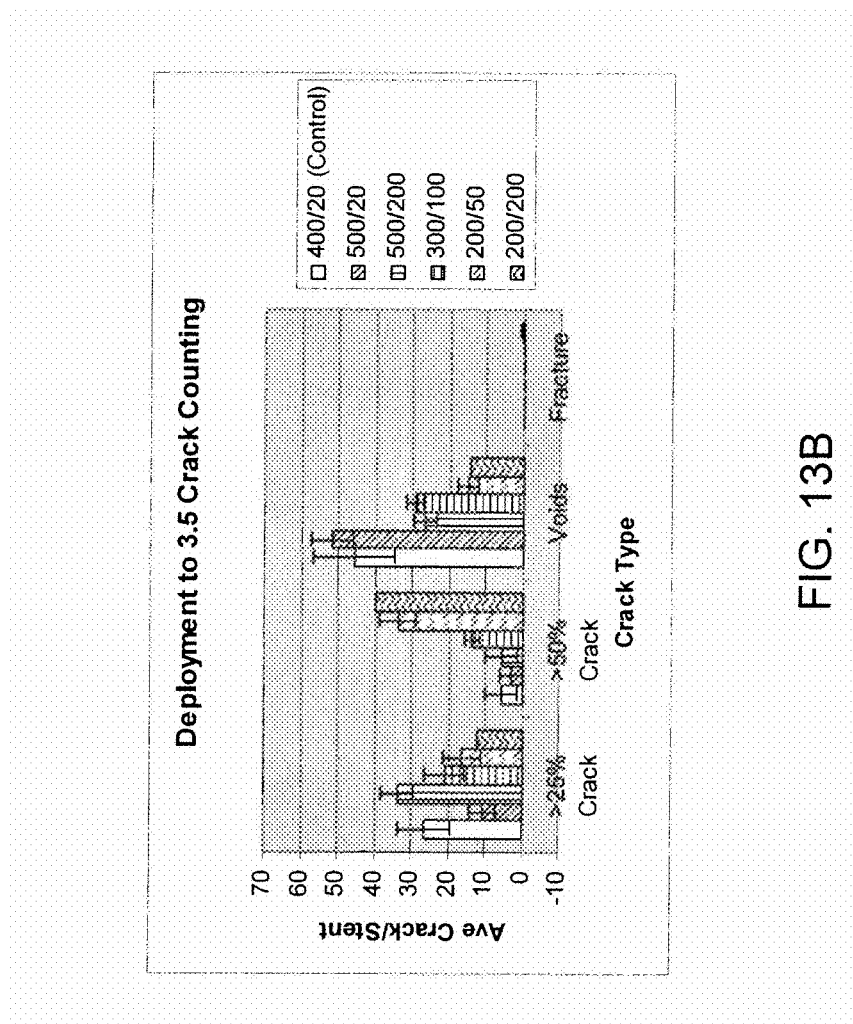

FIGS. 13A-B depict crack count results for the various groups of stents at 3 mm and 3.5 mm deployment. ">25% crack" refers to the number of cracks less than 25% of the width of a strut. For 3 mm deployment, 2 of 5 units in the 200/200 Group fractured (U crest). For 3.5 mm deployment, 2 of 3 remaining units in 200/200 Group fractured. Crack counts >50% tended to be higher for low radial expansion while voids tended to be higher for high radial strength.

Recoil of Stent

The percent recoil of the Groups was between 2 and 3%. Based on a model fit of the recoil data to the % RE and % AE, the percent recoil was a poor correlation ($R^2=0.32$) between the radial strength and the % RE and % AE.

Radial Stiffness of Stent

The radial stiffness of the stent for the groups exhibited trends similar to the radial strength.

Example 2

The following example illustrates the effect of temperature of the tube during deformation on the properties of a tube as a function of distance from the inside and outside surface. The properties measured were the modulus of elasticity and the hardness. The properties were measured using the Nano Indenter® G200 from Agilent Technologies, Inc. of Santa Clara, Calif. The properties of four samples listed in Table 2. Samples 1 and 2 have the same % RE and % AE and with two different deformation temperatures. Samples 3 and 4 have the same % RE and % AE and with two different deformation temperatures.

TABLE 2

Deformation temperatures and % RE/% AE for sample tested with Nanoindentation.

|  | Temperature | % RE/% AE |
| --- | --- | --- |
| Sample 1 | Low | 400/20 |
| Sample 2 | High | 400/20 |
| Sample 3 | Low |  |
| Sample 4 | 84° C. | 400/20 |

Figure 14A:
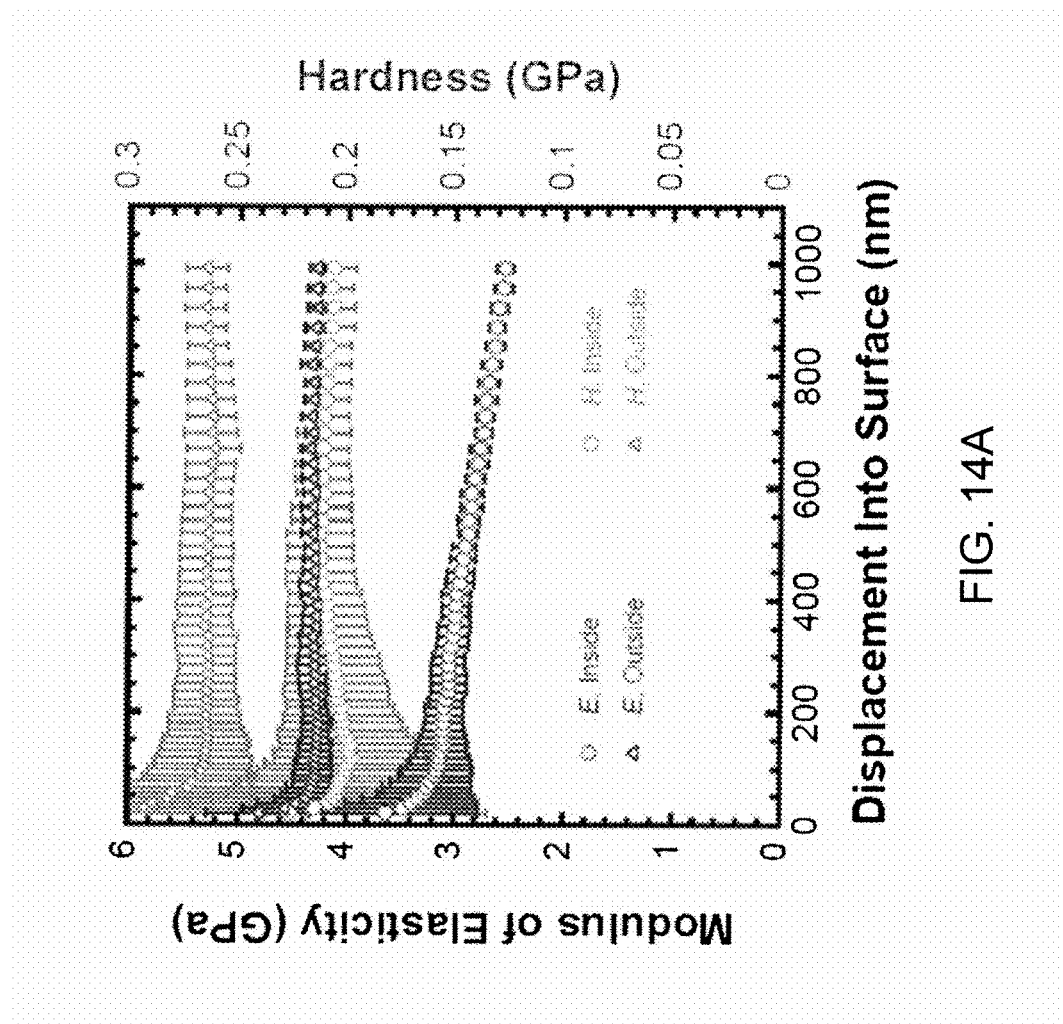
FIG. 14A shows a comparison between an elastic modulus and hardness as a function of distance from the inside and outside surfaces of a first sample of a radially deformed tube.
Figure 14B:
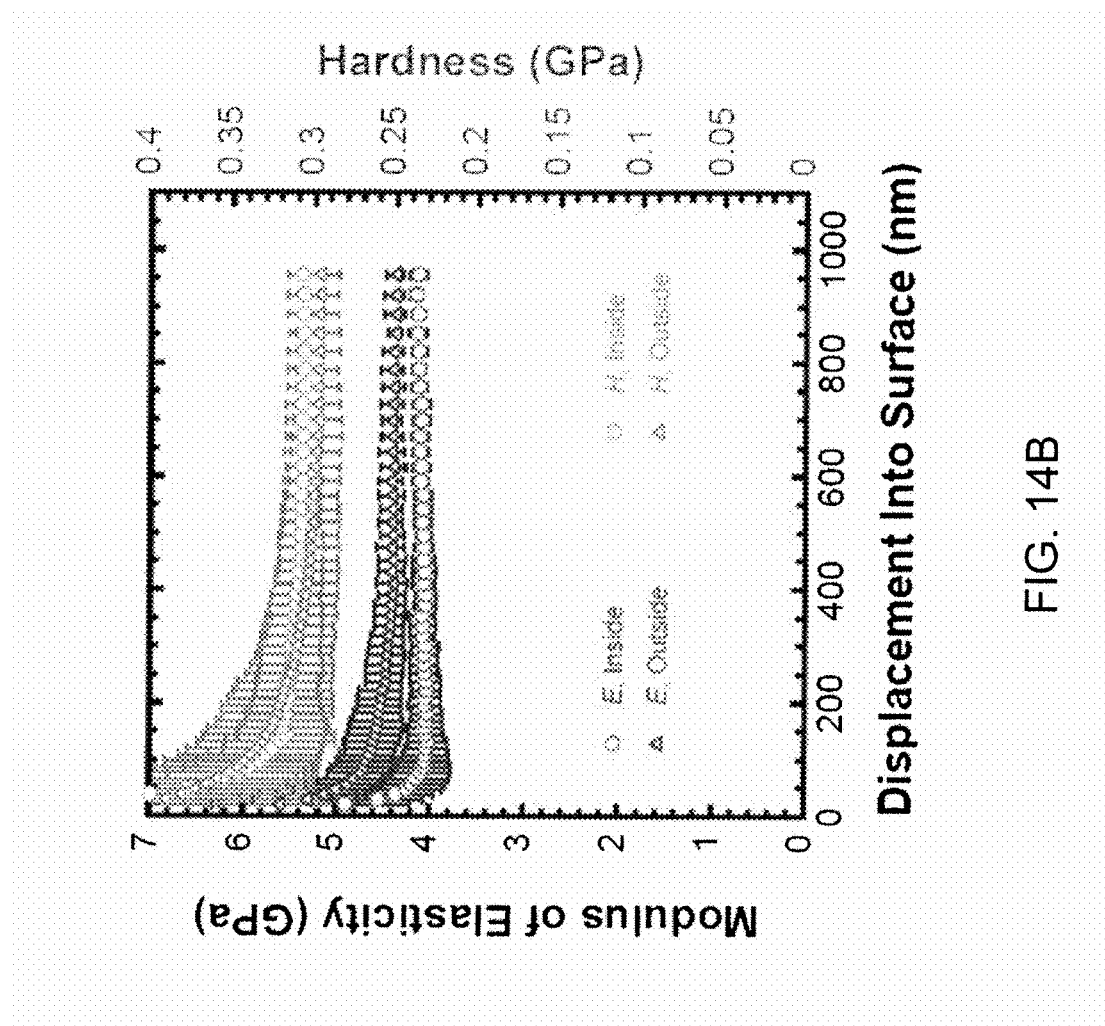
FIG. 14B shows a comparison between an elastic modulus and hardness as a function of distance from the inside and outside surfaces of a second sample of a radially deformed tube.
Figure 15A:
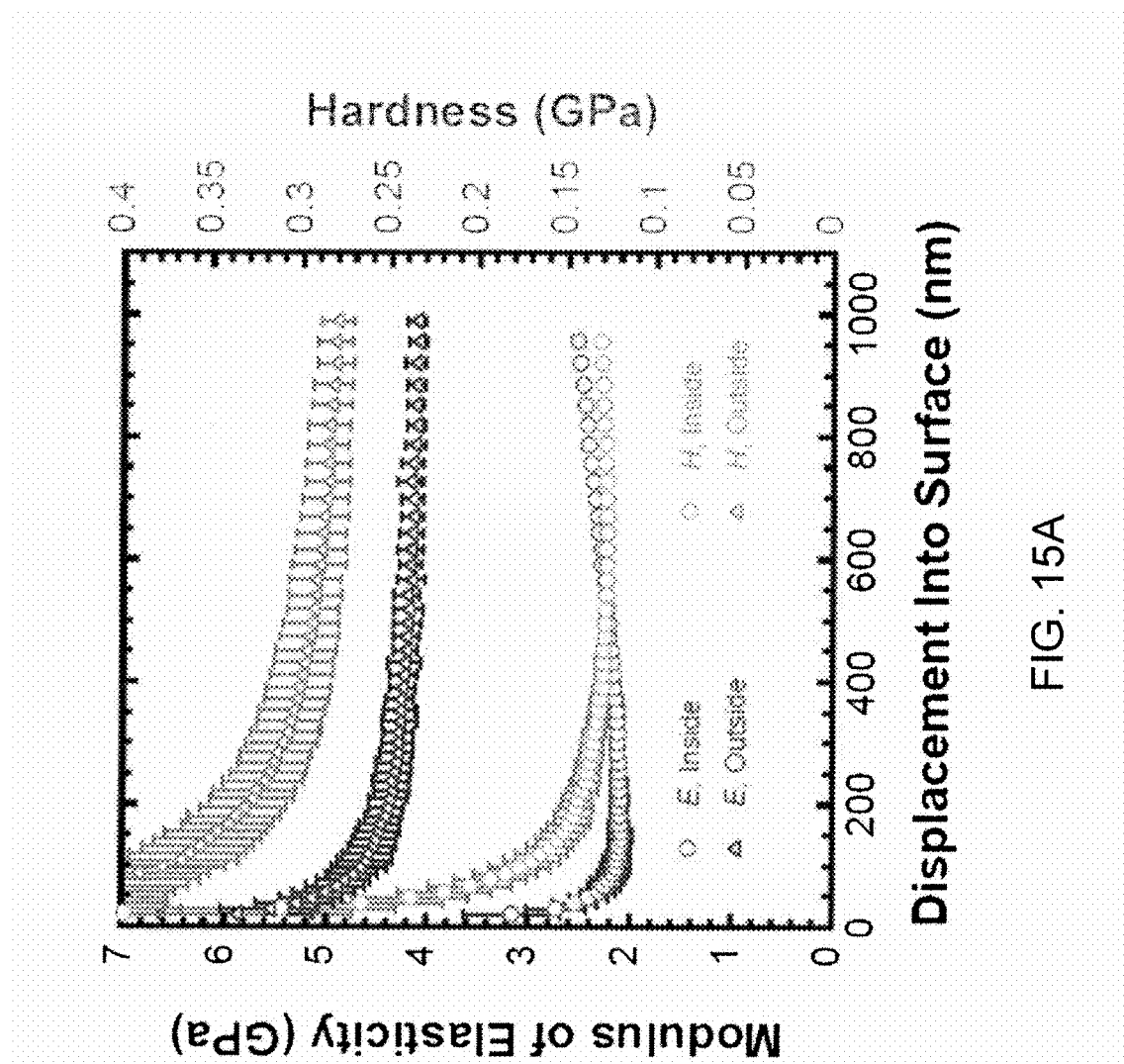
FIG. 15A shows a comparison between an elastic modulus and hardness as a function of distance from the inside and outside surfaces of a third sample of a radially deformed tube.
Figure 15B:
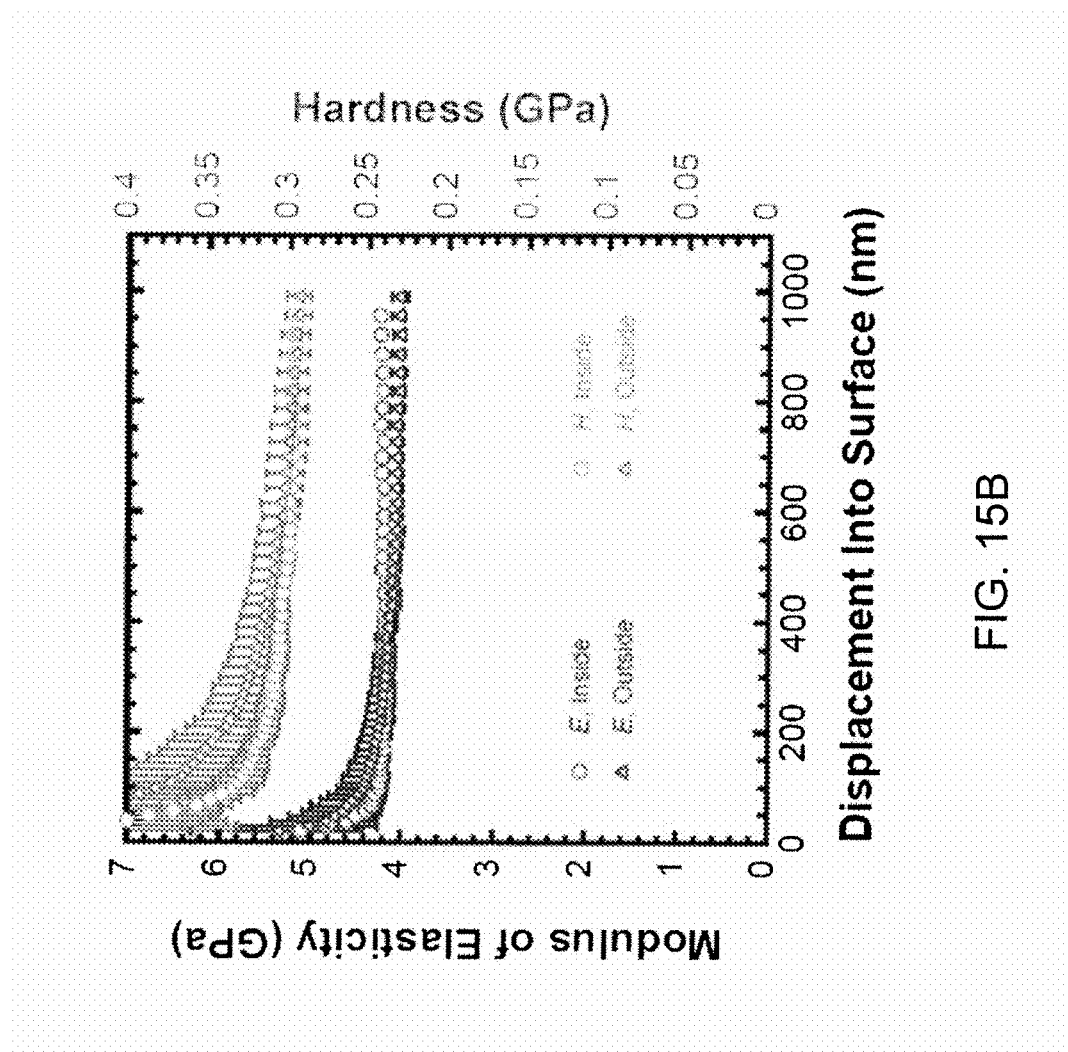
FIG. 15B shows a comparison between an elastic modulus and hardness as a function of distance from the inside and outside surfaces of a fourth sample of a radially deformed tube.

FIG. 14A compares the elastic modulus and hardness as a function of distance from the inside and outside surfaces of sample 1. FIG. 14B compares the elastic modulus and hardness as a function of depth from the inside and outside surfaces of sample 2. FIG. 15A compares the elastic modulus and hardness as a function of depth from the inside and outside surfaces of sample 3. FIG. 15B compares the elastic modulus and hardness as a function of depth from the inside and outside surfaces of sample 4.

The data in FIG. 14A shows that for sample 1 the hardness of the outside surface is approximately 33% higher than the hardness of the inside surface. The disparity in modulus increases as a function of depth, with the maximum occurring at 1 μm, where the modulus of the outside surface is approximately 75% higher than the modulus of the inside surface. The data in FIG. 14B shows that the inside and outside surfaces of sample 2 possesses very similar values of the elastic modulus and hardness.

The data in FIG. 15A shows that for sample 3 the modulus of the outside surface is approximately 63% higher than the modulus of the inside surface, and the hardness of the outside surface is approximately 115% higher than the hardness of the inside surface. The data FIG. 15B shows that the inside and outside surfaces of sample 4 posses very similar values of the elastic modulus and hardness.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a stent comprising:
    providing a tube made from a material comprising PLLA;
    radially and axially expanding the tube while the tube is heated to a processing temperature;
    wherein the processing temperature is 84° C. and the radial and axial expansion percentages are 400% and 20%, respectively, to produce an expanded tube having an increased strength, fracture toughness and homogeneity in a mechanical property over a wall thickness of the expanded tube; and
    forming the stent from the expanded tube.

2. The method of claim 1, wherein the tube is expanded using a pressure of 110-140 psi, heat nozzle speed of 0.32-1.0 mm/sec and pull speed of 0.58-3.8 mm/sec.

3. The method of claim 1, wherein the pattern forms a plurality of sinusoidal rings having crests and troughs, an angle of between 124 and 128 degrees at the crests, linking struts connecting the sinusoidal rings, the linking struts being parallel to a longitudinal axis of the deformed tube, and
wherein the linking struts and rings are arranged such that a closed cell is formed by a pair of longitudinally offset and adjacent rings and a pair of circumferentially offset and adjacent linking struts.

* * * * *